United States Patent [19]

Bridger

[11] 4,197,210

[45] Apr. 8, 1980

[54] OIL-SOLUBLE ADDUCTS OF BENZOTRIAZOLE AND DIALKYLAMINES AND LUBRICANT COMPOSITIONS CONTAINING THE SAME

[75] Inventor: Robert F. Bridger, Hopewell, N.J.

[73] Assignee: Mobil Oil Corporation, New York, N.Y.

[21] Appl. No.: 966,169

[22] Filed: Dec. 4, 1978

Related U.S. Application Data

[63] Continuation of Ser. No. 789,767, Apr. 22, 1977, abandoned.

[51] Int. Cl.$^2$ .............................................. C10M 1/32
[52] U.S. Cl. .................................... 252/50; 548/257; 548/262
[58] Field of Search ....................... 252/50; 260/308 B

[56] References Cited

U.S. PATENT DOCUMENTS

| | | | |
|---|---|---|---|
| 1,888,023 | 11/1932 | Adams | 252/50 X |
| 2,234,096 | 3/1941 | Teter et al. | 252/50 X |
| 2,758,086 | 8/1956 | Stuart et al. | 252/50 X |
| 3,265,620 | 8/1966 | Heiman | 252/50 X |
| 3,914,179 | 10/1975 | Byford et al. | 252/50 X |
| 3,923,672 | 12/1975 | Durr, Jr. et al. | 252/50 X |

Primary Examiner—Andrew Metz
Attorney, Agent, or Firm—Charles A. Huggett; Raymond W. Barclay; Howard M. Flournoy

[57] ABSTRACT

Certain new adducts of benzotriazole and dialkylamines, the alkyl groups of which contain from 4 to 20 carbon atoms, are provided. Lubricant compositions having excellent anticorrosion characteristics are also provided when minor amounts of such adducts are added thereto.

25 Claims, No Drawings

OIL-SOLUBLE ADDUCTS OF BENZOTRIAZOLE AND DIALKYLAMINES AND LUBRICANT COMPOSITIONS CONTAINING THE SAME

This is a continuation of copending application Ser. No. 789,767, filed Apr. 22, 1977, and now abandoned.

BACKGROUND OF THE INVENTION

1. Field of the Invention

This invention relates to a new addiitive composition constituting the reaction product adduct of benzotriazole and a specified dialkylamine.

This invention further relates to lubricant compositions which normally cause or induce oxidative deterioration and/or corrosion of metallic surfaces with which said compositions are in contact. More particularly, in one of its aspects, the invention relates to lubricant compositions, particularly petroleum derived compositions, such as mineral lubricating oils, automotive oils, gear oils, transmission fluids, hydraulic fluids, way lubricants, heavy circulating oils, greases and other forms of lubricant compositions normally requiring the presence of anticorrosion additives and which contain a minor proportion of the aforenoted additive.

2. Description of the Prior Art

Prior to the present invention, benzotriazole has been employed in lubricants as a metal deactivator. Benzotriazole-maleic anhydride adducts have also been known and are disclosed in "Elisa Shigi and Franca Rocchi," Gass. Chim. Ital. 84, 183 (1955). It is found, however, that these adducts are not effective anticorrosion agents inasmuch as they are not oil-soluble.

SUMMARY OF THE INVENTION

In accordance with the present invention, it has been found that anticorrosion properties can be effectively incorporated into lubricant compositions by including an anticorrosion amount of an adduct of benzotriazole and a specified dialkylamine. These adducts are soluble in organic compositions, such as the aforementioned lubricating oils, automotive oils, gear oils, transmission fluids, greases and other forms of lubricating compositions normally requiring the presence of anticorrosion additives and exhibit excellent anticorrosion properties.

Therefore, the invention herein described and claimed is more particularly drawn to an adduct of benzotriazole and a dialkylamine prepared by reacting benzotriazole with a suitable dialkylamine and to a lubricant composition comprising a major proportion of an oil of lubricating viscosity or grease prepared therefrom and a minor amount sufficient to impart anticorrosion properties thereto of said adduct.

The dialkylamines suitable herein include those having the general formula $R_1R_2NH$ where $R_1$ and $R_2$ are alkyl groups of 4 to 20 carbon atoms. The groups may be either identical or dissimilar, providing they contain a number of carbon atoms within the aforenoted range. Also, it is contemplated that $R_1+R_2$ may be cycloalkyl, in which instance the cycloalkyl group may contain from 4 to 40 carbon atoms. Thus, the dialkylamines can be symmetrical such as dioctylamine or unsymmetrical such as heptyloctylamine.

Exemplary of the dialkylamines useful in forming the described benzotriazole adduct are dioctylamine, didecylamine, didodecylamine and distearylamine.

The adduct can be effectively employed in any amount which is useful for imparting the desired degree of anticorrosion properties. In many applications, the adduct is effectively employed in an amount from about 0.001% to about 20%, by weight, and preferably in an amount from about 0.5% to about 5%, by weight, of the total weight of the lubricant composition.

In general, the adduct of benzotriazole and the specified dialkylamines are preferably reacted in a mole ratio of benzotriazole and dialkylamine of from about 1:1.5 to about 1:5. This reaction can be conducted at a temperature from about 80° C., to about 150° C. and preferably from about 90° C. to about 110° C.

The above-described benzotriazole-dialkylamine adducts, as previously mentioned, may be incorporated in any lubricating media, which may comprise, for example, liquid lubricating oils. These oils may be in the form of either a mineral oil or a synthetic oil in the form of a grease in which any of the aforementioned oils are employed as a vehicle. In general, mineral oils, employed as the lubricating or grease vehicle, may be of any suitable lubricating viscosity range, as for example, from about 45 SSU at 100° F. to about 6,000 SSU at 100° F., and, preferably, from about 50 to about 250 SSU at 210° F. These oils may have viscosity indexes varying from below zero to about 100 or higher. Viscosity indexes from about 70 to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, and phenoxy phenylethers.

DESCRIPTION OF SPECIFIC EMBODIMENTS

The following examples and comparative data will serve to illustrate the novel adducts of the present invention and their anticorrosion properties in organic media, particularly lubricant compositions, containing them.

EXAMPLE 1

A mixture of di-n-octylamine (3 grams) and benzotriazole (1 gram) was stirred at 95° C. for 5 minutes. The product was then tested for oil solubility and anticorrosion activity as described below.

EXAMPLE 2

The product was prepared and tested as described in Example 1, except that di-n-decylamine was substituted for di-n-octylamine.

EXAMPLE 3

The product was prepared and tested as described in Example 1, except that di-n-dodecylamine was substituted for di-n-octylamine.

EXAMPLE 4

The product was prepared and tested as described in Example 1, except that distearylamine was substituted for di-n-octylamine.

EXAMPLE 5

A mixture of di-n-octylamine (9 grams) and benzotriazole (1 gram) was stirred at 95° C. for 5 minutes. The product was then tested for oil solubility as described below.

EXAMPLE 6

The product was prepared and tested as in Example 5 except that di-n-dodecylamine was substituted for di-n-octylamine.

EXAMPLE 7

The product was prepared and tested as in Example 5 except that distearylamine was substituted for di-n-octylamine.

Solubility Tests

The additives were tested for solubility in a 150 SUS solvent-refined mineral oil by measuring the time required to dissolve at 65° C., and the time required for formation of haze at 25° C. All additives were tested at the 0.1% benzotriazole level. A comparison with unreacted benzotriazole is shown in Table 1 below.

Corrosion Tests

Representative additives were then evaluated with respect to their abilities to protect copper and steel against corrosion by elemental sulfur in oil. The oil blend used for testing the aforementioned was an Arabian Light 150 SUS oil containing 50 ppm of elemental sulfur. The Modified ASLE-64-9 Corrosion Test was used.

TABLE 1

| | Solubilities of Additives in Lubricating Oils | |
|---|---|---|
| Blend (in 150 SUS oil) | Time required to dissolve in oil at 65° C. (minutes) | Time required to form precipitate or haze at 25° C. (hours) |
| 0.4% Example 1 (0.1% benzotriazole) (0.3% di-n-octylamine) | 6 | >23 |
| 0.4% Example 2 (0.1% benzotriazole) (0.3% di-n-decylamine) | 5 | >23 |
| 0.4% Example 3 (0.1% benzotriazole) (0.3% di-n-dodecylamine) | 4 | >23 |
| 0.4% Example 4 (0.1% benzotriazole) (0.3% distearylamine) | 4 | >23 |
| 1% Example 5 (0.1% benzotriazole) (0.9% di-n-octylamine) | 3 | >168 |
| 1% Example 6 (0.1% benzotriazole) (0.9% di-n-dodecylamine) | 2 | >168 |
| 1% Example 7 (0.1% benzotriazole) (0.9% distearylamine) | 2 | 16 |
| 0.1% benzotriazole | >240 | >0.5 |

MODIFIED ASLE-64-9 CORROSION TEST
ASLE SLIDEWAY LUBRICANT ACCELERATED BREAKDOWN TEST

Place clean polished pieces[1] of copper and carbon steel rods (approximate 0.25 inches diameter by 3.0 inches long) in a 100-cc Griffin beaker containing 35 to 40 grams of oil sample. Put beaker and contents into an electric drying oven for 24 hours, maintaining a temperature of 210°±2° F. (99°±1° C.). Test period may be extended 72 hours, if necessary.

[1] Test specimen pieces must be freshly polished and placed in pentane for >30 minutes before using. These polished specimens must then be used within 30 minutes after the original 30-minute pentane deactivation period.

Test results:
Condition of Steel Rod
Condition of Copper Rod
Precipitate or Sludge
Evaporation Loss % Wt.

Specimens should be rated "as is" when removed from the oil (no washing); copper and steel rods are rated by comparing them and assigning the number from 1 (clean) to 10 (completely covered with corrosion) which most closely resembles their condition.

TABLE 2

| | Corrosion Test Results | |
|---|---|---|
| | Metal Specimen Rating | |
| Additive | Copper | Steel |
| None | 9 | 8 |
| 0.02% Benzotriazole | 9 | 3 |
| 0.04% Benzotriazole | 3 | 1 |
| 0.08% Example 1 (0.02% benzotriazole) (0.06% di-n-octylamine) | 3 | 5 |
| 0.08% Example 2 (0.02% benzotriazole) (0.06% di-n-decylamine) | 3 | 5 |
| 0.08% Example 3 (0.02% benzotriazole) (0.06% di-n-dodecylamine) | 4 | 5 |
| 0.08% Example 4 (0.02% benzotriazole) (0.06% distearylamine) | 3 | 5 |

The data summarized in the Tables clearly establish that lubricant compositions of effective anticorrosion characteristics are provided when the reaction product of benzotriazole and a dialkylamine as defined herein are added in minor amounts thereto.

It is apparent to those skilled in the art that the present invention has been described with reference to preferred emobidments and that departure therefrom can be effectively made and are within the scope of the specification.

What is claimed is:

1. Lubricant compositions comprising oils of lubricating viscosity or greases prepared therefrom, containing a minor amount sufficient to impart anticorrosion properties thereto of an oil-soluble adduct of benzotriazole and a dialkylamine having the general formula $R_1R_2NH$ where $R_1$ and $R_2$ are alkyl, the alkyl groups of which contain from 4 to 20 carbon atoms, prepared by reacting benzotriazole and said dialkylamine at a temperature of from about 80° to 150° C. in a mole ratio of benzotriazole to dialkylamine of about 1:1.5 to about 1:5, and thereafter recovering and adding said adduct to said compositions in minor effective amounts.

2. The composition of claim 1 where $R_1 + R_2$ is cycloalkyl of 4–40 carbon atoms.

3. The composition defined in claim 1 wherein said adduct is present in an amount from about 0.001% to about 20%, by weight.

4. The composition defined in claim 1 wherein said adduct is present in an amount from about 0.5% to about 5%, by weight.

5. The composition defined in claim 1 wherein said composition comprises an oil of lubricating viscosity.

6. The composition defined in claim 5 wherein said oil is a mineral oil.

7. The composition defined in claim 1 wherein said composition comprises a grease.

8. The composition defined in claim 1 wherein the dialkylamine is selected from the group consisting of dioctylamine, didecylamine, didodecylamine and distearylamine.

9. The composition defined in claim 8 wherein the dialkylamine is di-n-octylamine.

10. A compound constituting an adduct of benzotriazole and a dialkylamine, the alkyl groups of which contain 4 to 20 carbon atoms.

11. The compound of claim 10 wherein said dialkylamine is a cyclodialkylamine.

12. The compound of claim 10 wherein said dialkylamine is di-n-octylamine.

13. The compound of claim 10 wherein said dialkylamine is didecylamine.

14. The compound of claim 10 wherein said dialkylamine is didodecylamine.

15. The compound of claim 10 wherein said dialkylamine is distearylamine.

16. A method for preparing the compound of claim 10 which comprises reacting benzotriazole and said dialkylamine at a temperature of 80° to 150° C. in a mole ratio of benzotriazole to dialkylamine of about 1:1.5 to about 1:5.

17. The method of claim 16 wherein the reaction temperature is from 90°–110° C.

18. The method of claim 16 wherein said compound is a cycloalkylamine-benzotriazole adduct.

19. The method of claim 16 wherein the compound is an adduct of di-n-octylamine and benzotriazole.

20. The method of claim 16 wherein said compound is an adduct of didecylamine and benzotriazole.

21. The method of claim 16 wherein said compound is an adduct of didodecylamine and benzotriazole.

22. The method of claim 16 wherein said compound is an adduct of distearylamine and benzotriazole.

23. The composition defined in claim 8 wherein the dialkylamine is didecylamine.

24. The composition defined in claim 8 wherein the dialkylamine is didodecylamine.

25. The composition defined in claim 8 wherein the dialkylamine is distearylamine.

* * * * *